United States Patent [19]

Ehlert et al.

[11] Patent Number: 4,829,811
[45] Date of Patent: May 16, 1989

[54] FLUID TESTING APPARATUS AND METHOD

[75] Inventors: Mark C. Ehlert; James W. Mueller, both of Duncan, Okla.

[73] Assignee: Halliburton Company, Duncan, Okla.

[21] Appl. No.: 179,164

[22] Filed: Apr. 8, 1988

[51] Int. Cl.[4] .......................................... G01N 11/14
[52] U.S. Cl. ......................................... 73/59; 366/273
[58] Field of Search ...................... 73/59, 54; 366/273; 310/49 R, 154, 266

[56] References Cited

U.S. PATENT DOCUMENTS

| | | | |
|---|---|---|---|
| 2,603,087 | 7/1952 | Von Hortenau | 73/59 |
| 3,875,791 | 4/1975 | Fitzgerald et al. | 73/59 |
| 4,299,118 | 11/1981 | Gau et al. | 73/59 |
| 4,484,468 | 11/1984 | Gau et al. | 73/60 |
| 4,612,800 | 9/1986 | Erian | 73/54 |
| 4,622,846 | 11/1986 | Moon, Jr. et al. | 73/59 |

FOREIGN PATENT DOCUMENTS

| | | | |
|---|---|---|---|
| 0094319 | 11/1983 | European Pat. Off. | 73/59 |
| 1184119 | 12/1964 | Fed. Rep. of Germany | 73/59 |
| 2632076 | 1/1978 | Fed. Rep. of Germany | 73/59 |

OTHER PUBLICATIONS

SPE 9285, "Transition Time of Cement Slurries Between the Fluid and Set State" Fred L. Sabins, John M. Tinsley and David L. Sutton, 1980.

Primary Examiner—Stewart J. Levy
Assistant Examiner—Joseph W. Rokos
Attorney, Agent, or Firm—Joseph A. Walkowski; E. Harrison Gilbert, III; Mark E. McBurney

[57] ABSTRACT

A fluid testing apparatus comprises a container for holding a fluid to be tested and a member disposed within the container so that the member is rotatable within a fluid to be tested within the container. The container has a wall defining a cavity into which the member extends. A magnetically responsive rotor is mounted on this end of the member. Immediately adjacent the outside surface of this wall, a plurality of stator poles are secured so that a field generated in the stator poles directly interacts with the rotor across the wall to rotate the member. The rotor and stator poles are preferably of a stepper motor.

6 Claims, 1 Drawing Sheet

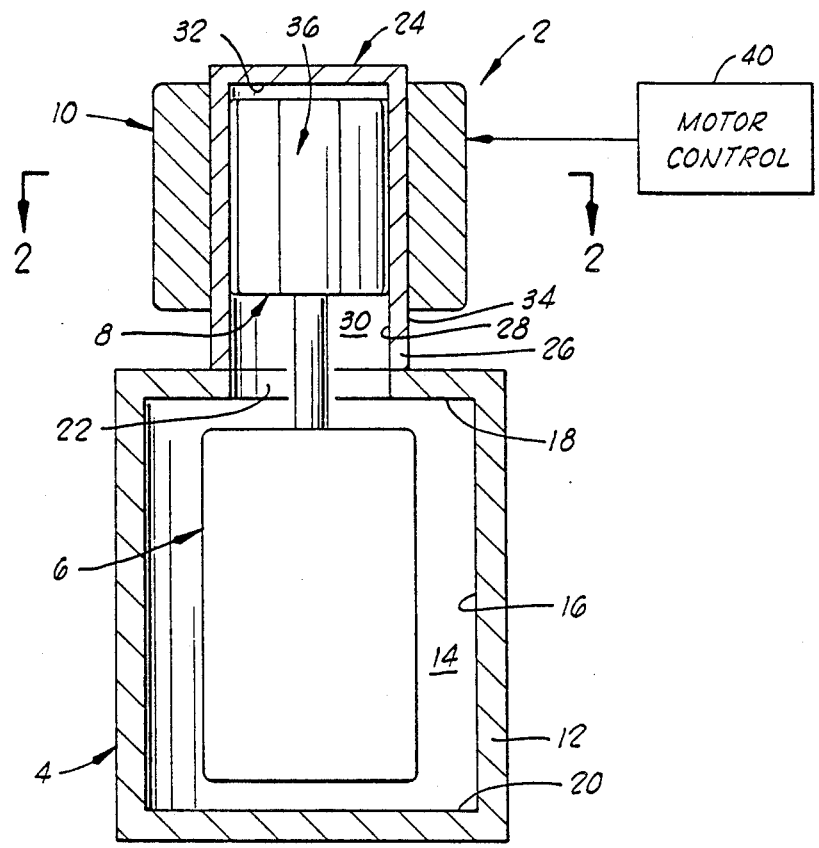
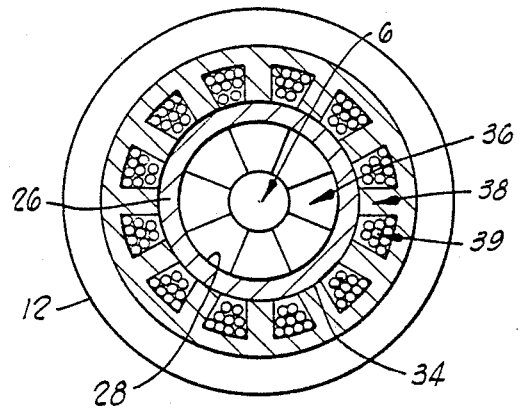
FIG. 1
FIG. 2

FLUID TESTING APPARATUS AND METHOD

BACKGROUND OF THE INVENTION

This invention relates generally to fluid testing apparatus and methods and more particularly, but not by way of limitation, to a device for imparting rotary motion to an object inside a pressure vessel.

In various industries there is the need for equipment and methods for testing fluids where some mixing or motion needs to be imparted to or within the fluid. For example, in the oil and gas industry, a fracturing fluid proposed to be used in a well bore to fracture a hydrocarbon-containing formation may need to be tested in a well-known device called a stirring autoclave. The fluid to be tested, comprising a mixture of substances, is introduced into the autoclave and then stirred to insure adequate mixing. Frequently, heat and pressure are then applied to simulate conditions in the well bore where the fluid is proposed to be used. Viscometers and consistometers are other examples in the oil and gas industry where a member or element inside a test chamber may need to be rotated to impart mixing or motion within the fluid. One technique for obtaining this motion is through a magnetic coupling/motor/endless belt assembly.

Although these types of equipment, such as the stirring autoclave, viscometer and consisoometer devices referred to above, have been known and used for a long time, we believe there is the need for an improvement in such equipment, namely, the improvement whereby the internal movable member is directly driven by, preferably, a stepper motor. Such an improvement should provide a relatively compact driving assembly. It should also provide highly accurate speed control of the movable member. This improvement should provide a more economical device, such as by replacing the aforementioned magnetic coupling/motor/endless belt assembly with a stepper motor.

SUMMARY OF THE INVENTION

The present invention provides the aforementioned improvements, namely, a compact, economical, accurately controllable fluid testing apparatus wherein an internal member is rotated directly by, in the preferred embodiment, a stepper motor.

For this preferred embodiment, the fluid testing apparatus comprises: containment means for holding a fluid to be tested, which containment means includes a wall defining a cavity within the containment means; a member disposed within the containment means so that the member is rotatable within a fluid to be tested within the containment means; and stepper motor means, mounted adjacent the wall of the containment means, for rotating the member in predetermined increments at selectable variable speeds, which stepper motor means includes: a plurality of permanent magnets disposed within the cavity of the containment means and connected to the member; and a plurality of stator poles secured to the wall in fixed relationship thereto so that a field generated in the stator poles directly interacts with the magnets across the wall to rotate the member.

The present invention also provides a method of stirring a fluid within a pressure vessel including a high-pressure bulkhead having a cylindrical wall, which wall includes an inner surface defining part of the cavity within the bulkhead and which wall includes an outer surface on the exterior of the bulkhead and the pressure vessel, which method comprises the steps of: mounting a rotor of a stepper motor on an end of a stirrer; inserting the stirrer into the pressure vessel so that the end of the stirrer with the rotor is disposed adjacent the inner surface of the cylindrical wall and within the cavity of the bulkhead and so that the stirrer is rotatable within the pressure vessel; mounting a stator, having a plurality of poles, of the stepper motor on the bulkhead adjacent the outer surface of the cylindrical wall in radial alignment with the rotor; and selectively energizing the poles of the stator to incrementally rotate the rotor and the stirrer at variable speeds.

Therefore, from the foregoing, it is a general object of the present invention to provide a novel and improved fluid testing apparatus and method. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 1 is a schematic illustration, in sectional elevation, of a stirring autoclave with a motor mounted for directly driving the stirrer of the autoclave.

FIG. 2 is a schematic sectional end view taken along line 2—2 shown in FIG. 1.

DETAILED DESCRIPTION OF THE PREFERRED EMBODIMENT

The preferred embodiment of a fluid testing apparatus 2 contemplated by us to provide the present invention is shown in FIGS. 1 and 2. Broadly, the fluid testing apparatus 2 includes containment means 4 for holding a fluid to be tested, a member 6 disposed within the containment means 4 so that the member 6 is rotatable within the fluid to be tested within the containment means 4, a magnetically responsive rotor 8 connected to the member 6, and a selectively energizable electromagnetic pole means 10 mounted outside of, but adjacent, the containment means 4 for magnetically driving the rotor 8 directly across the containment means 4 so that the rotor 8 and the member 6 rotate within the containment means 4.

The containment means 4 of the preferred embodiment is a pressure vessel which includes a cylindrical body 12 having a chamber 14 defined therein for receiving the test fluid under a pressure other than atmospheric pressure (typically a pressure greater than atmospheric pressure). The cavity 14 is defined by a cylindrical interior side surface 16 of the body 14 and between facing interior end surfaces 18, 20 of the body 12. An opening defined by a cylindrical surface 22 extends upwardly from the interior surface 18 through the upper wall of the body 12 as shown in FIG. 1.

This pressure vessel also includes a high-pressure bulkhead 24 having a cylindrical wall 26 extending upwardly from a suitable, known type of connection with the upper wall of the body 12. The wall 26 has an inner surface 28 defining part of a cavity 30 extending upwardly to an inner end surface 32 of the bulkhead 24. The wall 26 has a cylindrical outer surface 34 spaced from the inner surface 28 by a suitable thickness which provides adequate pressure retaining capability for the bulkhead 24. The illustrated connection of the bulkhead 24 to the body 12 is such that the cavity 30 extends from the chamber 14 at the opening 22. As shown in FIG. 1, this connection aligns the bulkhead 24 and the body 12 coaxially.

Suitably mounted in a manner known to the art within the chamber 14 and the cavity 30 is the member 6, which in the preferred embodiment is a conventional stirrer for stirring or rotating through the test fluid which is contained within the chamber 14 (the fluid is introduced into and removed from the chamber 14 by conventional means which are not illustrated in FIG. 1 but which are well known in the art). The conventional stirrer has a first end disposed in the cavity 30 and a second end disposed in the chamber 14 as shown in FIG. 1.

For the preferred embodiment of the present invention as schematically illustrated in FIGS. 1 and 2, the containment means 4 and the member 6 are characterized as a conventional stirring autoclave of the type used in the oil and gas industry for conducting various fluid tests, such as one or more known types of tests to be conducted on fracturing fluids.

Although the containment means 4 and the member 6 are conventional, they are combined in the present invention in a unique way with the magnetically responsive rotor 8 and the selectively energizable electromagnetic pole means 10 to achieve the advantages mentioned hereinabove. These advantages are achieved by using the direct drive established through the construction of the rotor 8 and the pole means 10 illustrated in FIGS. 1 and 2.

The magnetically responsive rotor 8 of the preferred embodiment includes a plurality of permanent magnets 36 disposed within the cavity 30 and connected to the upper end of the member 6. The magnets 36 of the preferred embodiment specifically define a permanent magnet rotor of a stepper motor. The magnets 36 are connected in an alternating north-pole, south-pole cylindrical array along a length of the cavity 30 within a preferred range of from greater than three inches to about six inches (it is contemplated, however, that other lengths may have utility). Although in FIG. 1 each of the magnets 36 is shown as a single elongated piece, different numbers and arrays of magnets can be used. By increasing the number of magnets disposed around the circumference of the rotor, a finer stepping increment construction can be obtained; but in any event the preferred embodiment rotor is moved in increments of predetermined magnitude based on the design of the specific stepper motor used.

In the preferred embodiment, the pole means 00 include a plurality of coil-wound stator poles 38 of the stepper motor (coil windings are identified by the reference numeral 39). The stator poles 38 are secured to the wall 26 in a fixed relationship thereto so that a moving electromagnetic field generated in the stator poles 38 directly interacts with the magnets 36 across the wall 26 to rotate the member 6. The field is generated in a known manner by a suitable stepper motor controller 40 of a known type. That is, the motor controller 40 provides means for operating the stepper motor at variable speeds independent of the viscosity of the test fluid. It is a conventional motor controller which gives accurate speed control over a large range of speeds.

The mounting of the stator poles 38 on the bulkhead 24 is by any suitable means for holding the stator adjacent the outer surface 34 of the wall 26 of the bulkhead 24. It is contemplated that conventional mounting brackets can be used. Such mounting will hold the inner diameter of the stator pole array a fixed radial distance from the outer diameter of the permanent magnet rotor 8. Because the wall 26 of the high-pressure bulkhead 24 must have an adequate thickness to withstand the internal pressure exerted against it in the exemplary environment of a pressurized stirring autoclave, it is contemplated that the spacing between the outer diameter of the rotor 8 and the inner diameter of the stator pole means 10 will be greater than would normally be found in a stepper motor and preferably within the range of radial distances from about 0.25 inch to about 0.67 inch (it is contemplated here, also, that other spacings may be accommodated). This spacing will be substantially filled by the thickness of the wall 26.

Although the preferred embodiment of the stepper motor has been described as including a permanent magnet rotor, from which one might infer that a particularly suitable type of stepper motor is one referred to as a permanent magnet stepper motor, it is contemplated that other types, such as a variable reluctance stepper motor or a hybrid stepper motor, can be used. Basically, however, the motor is to be one which can be mounted as illustrated in tee drawings and controlled to provide variable or selectable speeds of rotation regardless of the viscosity of the fluid to be tested. A stepper motor is a particularly suitable type of motor to provide this.

To use the apparatus 2, the motor controller 40 is appropriately controlled to generate the moving electromagnetic field in the stator means 10. This field effectively creates a rotating magnetic field which the magnets 36 of the rotor 8 follow in a circular manner so that the member 6 connected to the rotor 8 rotates with the rotor 8.

Through this construction and use, a method of stirring a fluid is provided. This method in the preferred embodiment includes mounting the rotor 8 of the stepper motor on an end of the stirrer 6; inserting the stirrer 6 into the pressure vessel so that the end of the stirrer 6 with the rotor 8 is disposed adjacent th inner surface 28 of the cylindrical wall 26 of the high-pressure bulkhead 24 of the pressure vessel and within the cavity 30 of the bulkhead 24 and so that the stirrer 6 is rotatable within the pressure vessel; mounting the stator, having the plurality of poles 38, of the stepper motor on the bulkhead 24 adjacent the outer surface 34 thereof in radial alignment with the rotor 8; and selectively energizing the poles 38 of the stator to incrementally rotate the rotor 8 and the stirrer 6 at variable speeds.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. A fluid testing apparatus, comprising:
   containment means for holding a fluid to be tested, said containment means including a wall defining a cavity within said containment means;
   a member disposed within said containment means so that said member is rotatable within a fluid to be tested within said containment means; and
   stepper motor means, mounted adjacent said wall of said containment means, for rotating said member in predetermined increments at selectable variable speeds, said stepper motor means including:

a plurality of permanent magnets disposed within said cavity of said containment means and connected to said member; and a plurality of stator poles secured to the exterior of said wall in fixed relationship thereto so that a field generated in said stator poles directly interacts with said magnets across said wall to rotate said member.

2. An apparatus as defined in claim 1, wherein said stator poles are spaced from said magnets across said wall by a radial distance within the range from about 0.25 inch to about 0.67 inch.

3. An apparatus as defined in claim 1, wherein said magnets are disposed in an alternating north-pole, south-pole cylindrical array along a length of said cavity within the range from greater than 3 inches to about 6 inches.

4. A fluid testing apparatus, comprising:

a pressure vessel including:

a body having a chamber defined therein for receiving a test fluid under a pressure greater than atmospheric pressure; and a high-pressure bulkhead having a cavity defined therein, said high-pressure bulkhead connected to said body so that said cavity extends from said chamber;

a stirrer including a first end disposed in said cavity of said high-pressure bulkhead and further including a second end disposed in said chamber of said body;

a magnetically responsive rotor connected to said first end of said stirrer; and selectively energizable electromagnetic pole means, fixedly mounted adjacent said high-pressure bulkhead outside of said cavity thereof, for electromagnetically driving said rotor directly across said high-pressure bulkhead so that said rotor and said stirrer rotate within said pressure vessel.

5. An apparatus as defined in claim 4, wherein:

said rotor is characterized as a permanent magnet rotor of a stepper motor;

said pole means defines a stator of said stepper motor; and said apparatus further comprises means for operating said stepper motor at variable speeds independent of the viscosity of the test fluid.

6. A method of stirring a fluid within a pressure vessel including a high-pressure bulkhead having a cylindrical wall, which wall includes an inner surface defining part of a cavity within the bulkhead and which wall includes an outer surface on the exterior of the bulkhead and the pressure vessel, said method comprising the steps of:

mounting a rotor of a stepper motor on an end of a stirrer;

inserting the stirrer into the pressure vessel so that the end of the stirrer with the rotor is disposed adjacent the inner surface of the cylindrical wall and within the cavity of the bulkhead and so that the stirrer is rotatable within the pressure vessel;

mounting a stator, having a plurality of poles, of the stepper motor on the bulkhead adjacent the outer surface of the cylindrical wall in radial alignment with the rotor; and selectively energizing the poles of the stator to incrementally rotate the rotor and the stirrer at variable speeds.

* * * * *

UNITED STATES PATENT AND TRADEMARK OFFICE
CERTIFICATE OF CORRECTION

PATENT NO. : 4,829,811

DATED : May 16, 1989

INVENTOR(S) : Mark C. Ehlert and James W. Mueller

It is certified that error appears in the above-identified patent and that said Letters Patent is hereby corrected as shown below:

In column 1, line 28, the word "consisoometer" should read --consistometer--,

In column 3, line 49, the word "00" should read --10--,

In column 4, line 22, the word "tee" should read --the--,

In column 4, line 39, the word "th" should read --the--,

Signed and Sealed this

Thirtieth Day of January, 1990

Attest:

JEFFREY M. SAMUELS

Attesting Officer     Acting Commissioner of Patents and Trademarks